(12) United States Patent
Gofman

(10) Patent No.: US 9,673,612 B2
(45) Date of Patent: Jun. 6, 2017

(54) REVERSE BATTERY PROTECTION FOR BATTERY-POWERED DEVICES

(71) Applicant: ASCENSIA DIABETES CARE HOLDINGS AG, Basel (CH)

(72) Inventor: Igor Gofman, Croton-on-Hudson, NY (US)

(73) Assignee: ASCENSIA DIABETES CARE HOLDINGS AG, Basel (CH)

( * ) Notice: Subject to any disclaimer, the term of this patent is extended or adjusted under 35 U.S.C. 154(b) by 0 days.

(21) Appl. No.: 15/068,524

(22) Filed: Mar. 11, 2016

(65) Prior Publication Data

US 2016/0241015 A1 Aug. 18, 2016

Related U.S. Application Data

(63) Continuation of application No. 13/796,890, filed on Mar. 12, 2013, now Pat. No. 9,300,129.

(51) Int. Cl.
*H02H 3/18* (2006.01)
*H02H 11/00* (2006.01)
(Continued)

(52) U.S. Cl.
CPC ......... *H02H 3/18* (2013.01); *G01N 33/48785* (2013.01); *G01N 33/49* (2013.01); *H02H 11/002* (2013.01); *H02H 11/003* (2013.01)

(58) Field of Classification Search
CPC ...... H02H 11/002; H02H 3/18; H02H 11/003; G01N 33/48785; G01N 33/49
See application file for complete search history.

(56) References Cited

U.S. PATENT DOCUMENTS 4,303,958 A 12/1981 Allgood
4,423,456 A 12/1983 Zaidenweber
(Continued)

FOREIGN PATENT DOCUMENTS

WO  WO 00/02134    1/2000
WO  WO 2012/110913  8/2012
WO  WO 2015/120339  8/2015

OTHER PUBLICATIONS

International Search Report and Written Opinion in counterpart International Application No. PCT/US2014/021146 mailed Jun. 12, 2014.
(Continued)

*Primary Examiner* — Zeev V Kitov
(74) *Attorney, Agent, or Firm* — Dugan & Dugan, PC

(57) ABSTRACT

Reverse battery protection circuits for devices powered by batteries coupled in parallel can include both P-channel and N-channel MOSFETs. Each positive battery terminal connector of a battery-powered device can be coupled to a gate of an N-channel MOSFET or to both a gate of an N-channel MOSFET and a gate of a P-channel MOSFET. In some embodiments, each negative battery terminal connector of the device can be connected to a gate of a P-channel MOSFET. In the event of a reverse battery connection, one or more of the protection circuit's P-channel and N-channel MOSFETS can switch to a non-conductive state to isolate the device's load from an incorrectly installed battery and prevent the incorrectly installed battery and/or other parallel-coupled battery from prematurely discharging. Methods of protecting a load from a reverse battery connection are also provided, as are other aspects.

14 Claims, 11 Drawing Sheets

(51) Int. Cl.
*G01N 33/487* (2006.01)
*G01N 33/49* (2006.01)

(56) References Cited

U.S. PATENT DOCUMENTS

| | | |
|---|---|---|
| 5,623,550 A | 4/1997 | Killion |
| 5,870,031 A | 2/1999 | Kaiser et al. |
| 7,561,404 B2 | 7/2009 | Sells |
| 2007/0115706 A1 | 5/2007 | Sells |
| 2013/0313917 A1 | 11/2013 | Finlayson et al. |
| 2014/0268455 A1 | 9/2014 | Gofman |

OTHER PUBLICATIONS

International Search Report and Written Opinion in counterpart International Application No. PCT/US2015/014925 mailed Apr. 23, 2015.

International Preliminary Report on Patentability in counterpart International Application No. PCT/US2014/021146 mailed Sep. 24, 2015.

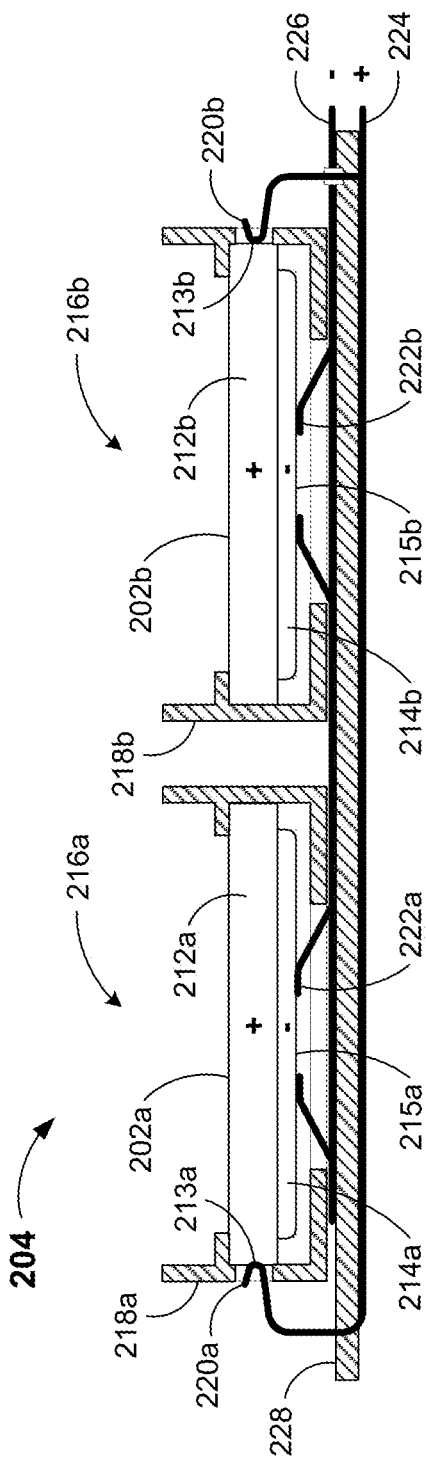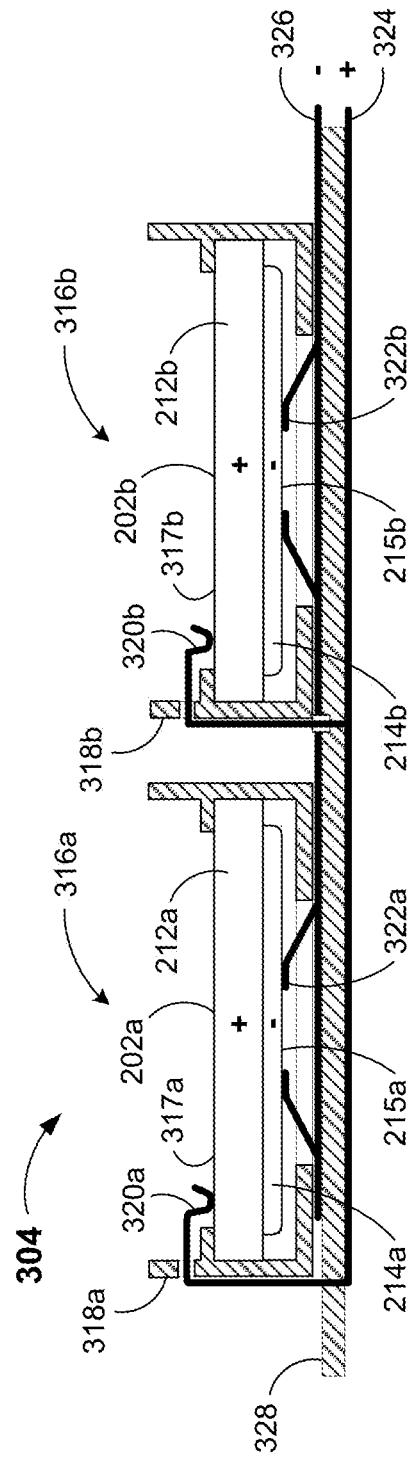

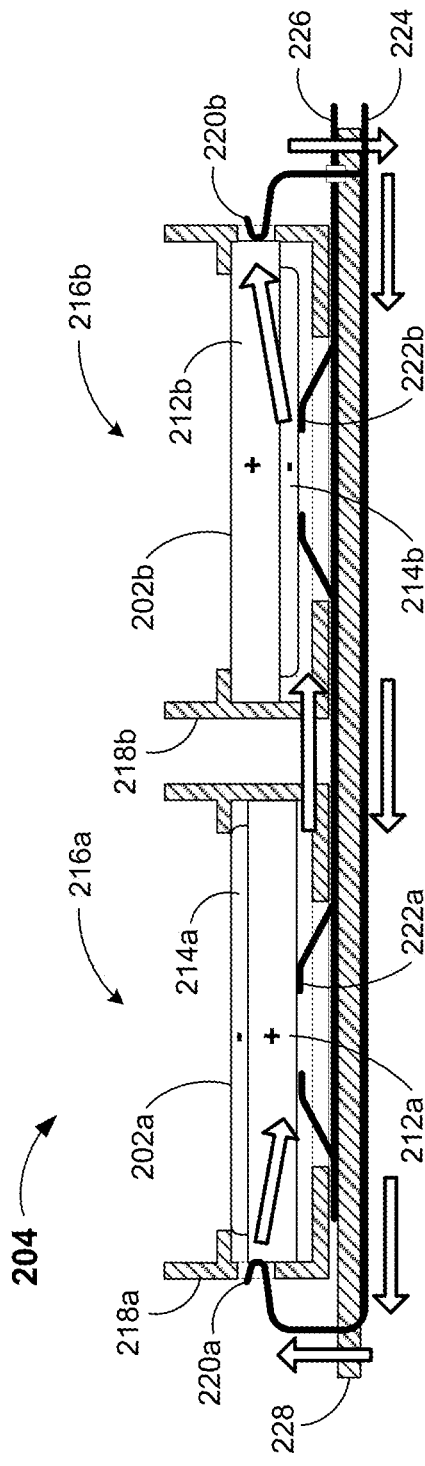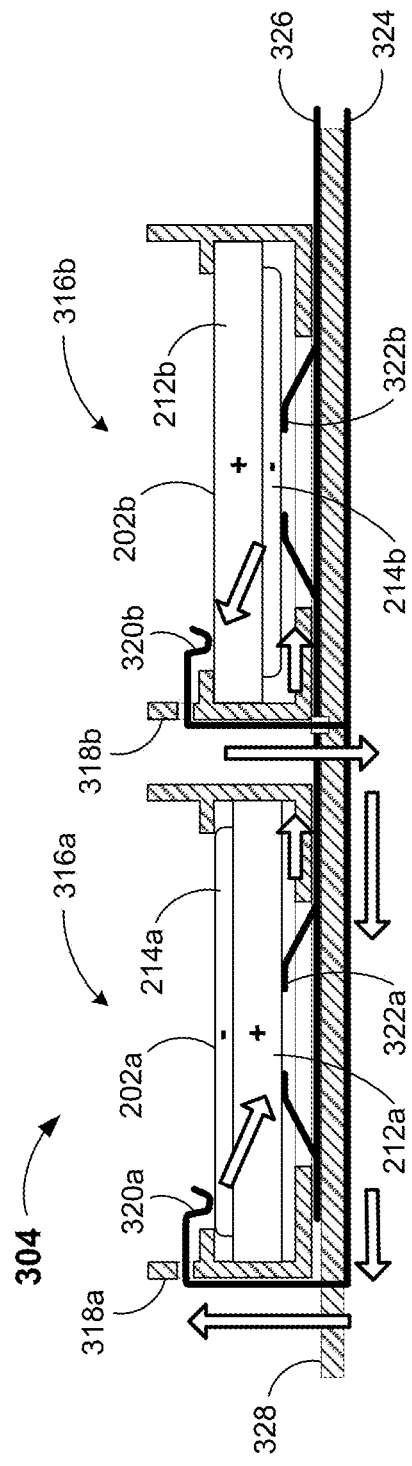

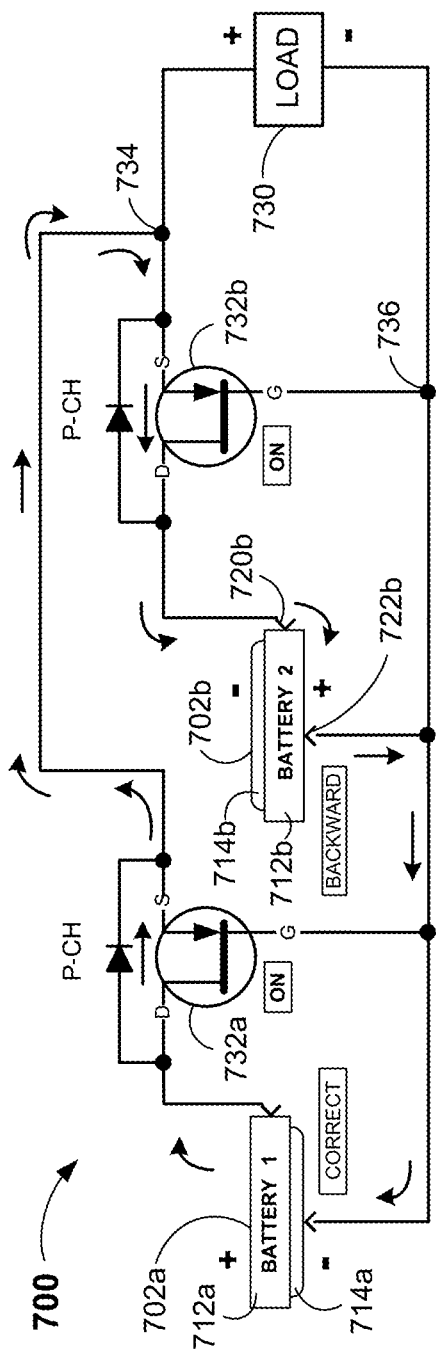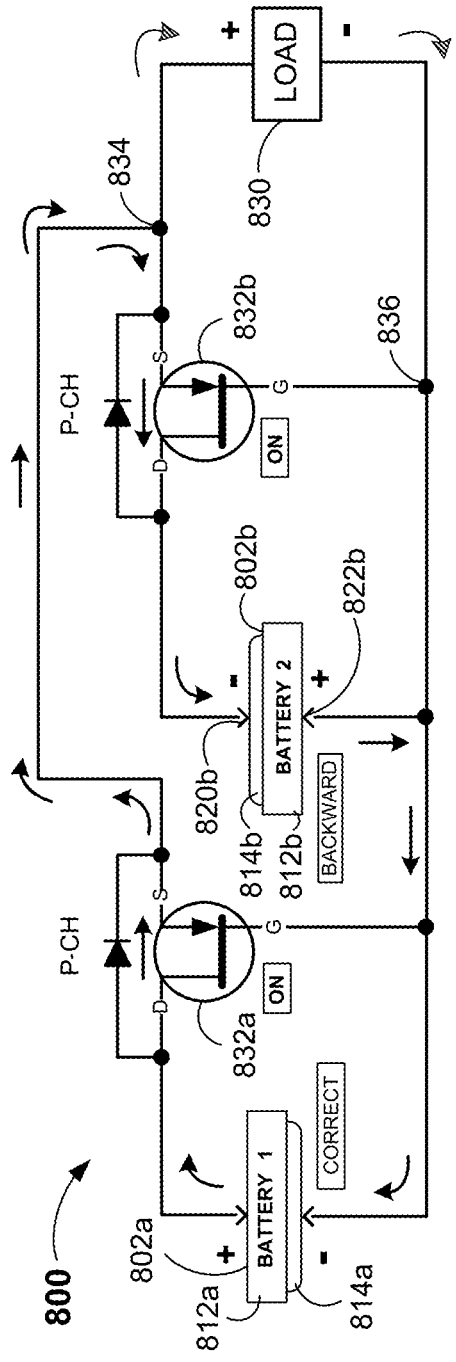
FIG. 7
PRIOR ART
FIG. 8
PRIOR ART

REVERSE BATTERY PROTECTION FOR BATTERY-POWERED DEVICES

RELATED APPLICATIONS

The present application is a continuation of U.S. Non-Provisional application Ser. No. 13/796,890 filed Mar. 12, 2013, entitled "REVERSE BATTERY PROTECTION FOR BATTERY-POWERED DEVICES", which is hereby incorporated by reference herein in its entirety for all purposes.

FIELD

The invention relates generally to battery-powered devices, and more particularly to devices powered by batteries coupled in parallel.

BACKGROUND

Coupling batteries in parallel is a common method of providing more power to a load. For example, some known portable blood glucose meters require two batteries coupled in parallel to power the meter's load (e.g., electronics). Accidental reverse battery installation in such devices can cause one or more problems including abnormal device operation, damage to the device's load, and/or premature battery discharge. Some devices employ mechanical safeguards, such as, e.g., special battery connectors, to prevent inadvertent reverse battery installation. However, mechanical safeguards can be expensive and/or may not be effective with certain kinds of batteries, such as, e.g., coin or lithium cell type batteries. Some devices employ circuitry to protect against reverse battery installation. However, some known protection circuits, such as those using diodes, can result in undesirable power losses. Other known protection circuits, such as those using MOSFETs (metal-oxide-semiconductor-field-effect-transistors), may not be effective in devices powered by parallel-coupled batteries. In particular, the type of batteries and/or the type of parallel-battery holders and/or connectors used in a device can render some known MOSFET protection circuits ineffective. Thus, a need still exists to provide reverse battery protection for devices powered by batteries coupled in parallel.

SUMMARY

According to one aspect, a reverse battery protection circuit is provided. The reverse battery protection circuit comprises a first load terminal, a second load terminal, a first P-channel MOSFET having a drain, a gate, and a source coupled to the first load terminal, a first N-channel MOSFET having a drain, a gate, and a source coupled to the second load terminal, a first positive battery terminal connector coupled to the drain of the first P-channel MOSFET and to the gate of the first N-channel MOSFET, the first positive battery terminal connector configured to electrically connect to a first battery terminal, and a first negative battery terminal connector coupled to the drain of the first N-channel MOSFET and to the gate of the first P-channel MOSFET, the first negative battery terminal connector configured to electrically connect to a second battery terminal.

According to another aspect, a reverse battery protection circuit is provided that comprises a first P-channel MOSFET having a gate, a drain, and a source; a second P-channel MOSFET having a gate, a drain coupled to the gate of the first P-channel MOSFET, and a source coupled to the source of the first P-channel MOSFET; a first N-channel MOSFET having a gate coupled to the gate of the second P-channel MOSFET, a drain coupled to the drain of the second P-channel MOSFET and to the gate of the first P-channel MOSFET, and a source; a first load terminal coupled to the drain of the first P-channel MOSFET; a first positive battery terminal connector coupled to the source of the first P-channel MOSFET and to the source of the second P-channel MOSFET, the first positive battery terminal connector configured to electrically connect to a first battery terminal; a second positive battery terminal connector coupled to the gate of the first N-channel MOSFET and to the gate of the second P-channel MOSFET, the second positive battery terminal connector configured to electrically connect to a second battery terminal; a first negative battery terminal connector configured to electrically connect to a third battery terminal; a second negative battery terminal connector configured to electrically connect to a fourth battery terminal; and a second load terminal; wherein the first negative battery terminal, the second negative battery terminal, the second load terminal, and the source of the first N-channel MOSFET are coupled to each other.

According to a further aspect, a method of protecting a load from a reverse battery connection is provided. The method comprises coupling a source of a first P-channel MOSFET to a first load terminal, coupling a source of a first N-channel MOSFET to a second load terminal, coupling a first positive battery terminal connector to a drain of the first P-channel MOSFET and to a gate of the first N-channel MOSFET, the first positive battery terminal configured to electrically connect to a first battery terminal, and coupling a first negative battery terminal connector to a drain of the first N-channel MOSFET and to a gate of the first P-channel MOSFET, the first negative battery terminal configured to electrically connect to a second battery terminal.

According to a still further aspect, another method of protecting a load from a reverse battery connection is provided. The method comprises coupling a gate of a first P-channel MOSFET to a drain of a second P-channel MOSFET and to a drain of a first N-channel MOSFET, coupling a drain of the first P-channel MOSFET to a first load terminal, coupling a source of the first P-channel MOSFET to a source of the second P-channel MOSFET and to a first positive battery terminal connector, the first positive battery terminal connector configured to electrically connect to a first battery terminal, coupling a gate of the second P-channel MOSFET to a gate of the first N-channel MOSFET and to a second positive battery terminal connector, the second positive battery terminal connector configured to electrically connect to a second battery terminal, and coupling a source of the first N-channel MOSFET to a first negative battery terminal connector, to a second negative battery terminal connector, and to a second load terminal; wherein the first negative battery terminal connector is configured to electrically connect to a third battery terminal, and the second negative battery terminal connector is configured to electrically connect to a fourth battery terminal.

Still other aspects, features, and advantages of the invention may be readily apparent from the following detailed description wherein a number of example embodiments and implementations are described and illustrated, including the best mode contemplated for carrying out the invention. The invention may also include other and different embodiments, and its several details may be modified in various respects, all without departing from the scope of the invention. Accordingly, the drawings and descriptions are to be regarded as illustrative in nature, and not as restrictive. The drawings are not necessarily drawn to scale. The invention covers all modifications, equivalents, and alternatives falling within the scope of the invention.

BRIEF DESCRIPTION OF DRAWINGS

The skilled artisan will understand that the drawings, described below, are for illustration purposes only. The drawings are not intended to limit the scope of the disclosure in any way.

FIG. 2 illustrates a cross-sectional side view of a side-contact battery holder configured to receive a pair of coin or lithium cell batteries coupled in parallel according to the prior art.

FIG. 3 illustrates a cross-sectional side view of a top-contact battery holder configured to receive a pair of coin or lithium cell batteries coupled in parallel according to the prior art.

FIG. 4 illustrates a cross-sectional side view of the side-contact battery holder of FIG. 2 with a reverse-connected battery.

FIG. 5 illustrates a cross-sectional side view of the top-contact battery holder of FIG. 3 with a reverse-connected battery.

FIG. 7 illustrates a schematic circuit diagram of a side-contact battery circuit with a reverse-connected battery according to the prior art.

FIG. 8 illustrates a schematic circuit diagram of a top-contact battery circuit with a reverse-connected battery according to the prior art.

DESCRIPTION

Reference will now be made in detail to the example embodiments of this disclosure, which are illustrated in the accompanying drawings. Wherever possible, the same reference numbers will be used throughout the drawings to refer to the same or like parts.

In one aspect, the load (e.g., electronics or circuitry) of a battery-powered device can be protected from a reverse battery connection by a protection circuit incorporated in the device. The protection circuit can include both P-channel and N-channel MOSFETs (metal-oxide-semiconductor-field-effect-transistors), wherein at least some of the gates of those P-channel and N-channel MOSFETs can be coupled directly (i.e., with no intervening device(s) or circuit component(s) excluding resistive elements) to the battery terminal connectors of the device. In some embodiments, each positive battery terminal connector in a device can be connected to a gate of a respective N-channel MOSFET or to both a gate of a respective P-channel MOSFET and a gate of a respective N-channel MOSFET, depending on the type of battery connectors used in the device. In some embodiments, each negative battery terminal connector in a device can be connected to a gate of a respective P-channel MOSFET. In the event of a reverse battery connection, at least one P-channel MOSFET and at least one N-channel MOSFET can switch into a non-conductive state (i.e., they each "turn off"). The switching into non-conductive states can isolate, and therefore protect, a device's load from an incorrectly installed battery. The protection circuit can also prevent an incorrectly installed battery, and/or other battery coupled in parallel with the incorrectly installed battery, from prematurely discharging. In other aspects, methods of protecting a load from a reverse battery connection are provided, as will be explained in greater detail below in connection with FIGS. 1-14.

Figure 1:
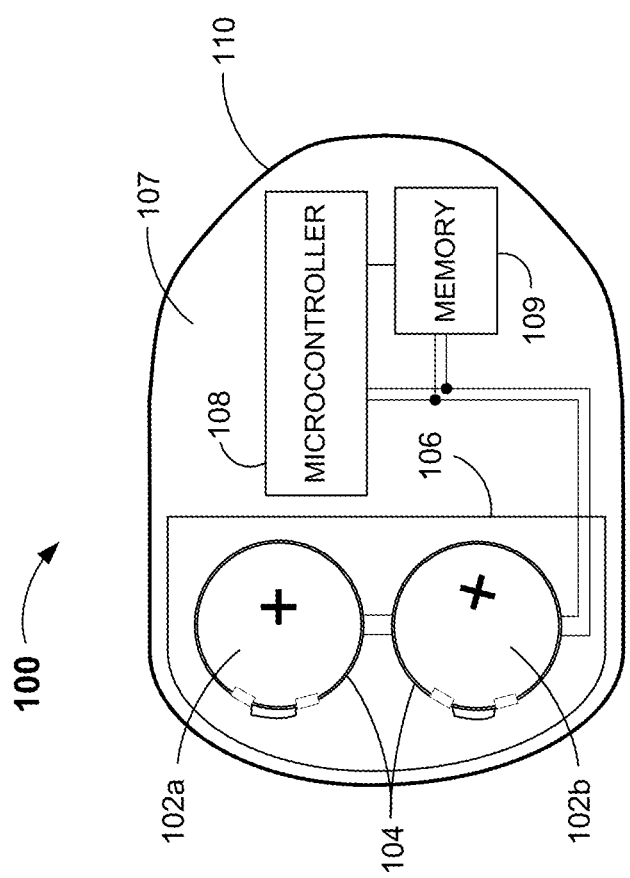
FIG. 1 illustrates a simplified top schematic view of an example biosensor meter powered by a pair of batteries coupled in parallel according to the prior art.

FIG. 1 illustrates an example of a known device, a biosensor meter 100, powered by batteries coupled in parallel according to the prior art. Biosensor meter 100 can be powered by first and second batteries 102a and 102b coupled in parallel and seated in a battery holder 104. First and second batteries 102a and 102b can be identical and can each be, e.g., a coin or lithium cell type battery, such as, e.g., a 3-volt CR2032 battery. Battery holder 104 can be located in a battery compartment 106, which can be accessible from the back 107 of biosensor meter 100. Biosensor meter 100 can also include a microcontroller 108 and a memory 109 powered by first and second batteries 102a and 102b. Microcontroller 108 can be configured to determine a property of an analyte in a fluid, such as, e.g., a concentration of blood glucose in a sample of blood, and memory 109 can be configured to store measurement results. Microcontroller 108 can be a conventional microcontroller, such as, e.g., a V850 microcontroller by Renesas Electronics America Inc., of Santa Clara, Calif., or another similar microcontroller. Other components of biosensor meter 100 can include, e.g., input/output devices, a display, and a test sensor port (none shown), all of which can be powered by first and second batteries 102a and 102b. Microcontroller 108, memory 109, and the other electrical components of biosensor meter 100 can be considered the "load" powered by first and second batteries 102a and 102b. A housing 110 can be configured to house therein first and second batteries 102a and 102b, battery holder 104, battery compartment 106, microcontroller 108, memory 109, and the other components of biosensor meter 100. An example of a biosensor meter 100 can be the CONTOUR® USB Blood Glucose Meter by Bayer Healthcare, of Tarrytown, N.Y.

FIGS. 2 and 3 illustrate two known types of battery holders 204 and 304, respectively, that can each be used in, e.g., biosensor meter 100, as well as in other battery-powered devices requiring parallel-coupled batteries, according to the prior art. Battery holders 204 and 304 can each be configured to receive and couple in parallel first and second batteries 202a and 202b. First and second batteries 202a and 202b can each be identical coin or lithium cell batteries, wherein first battery 202a can have a first positive battery terminal 212a and a first negative battery terminal 214a, and second battery 202b can have a second positive battery terminal 212*b* and a second negative battery terminal 214*b*. First positive battery terminal 212*a* and first negative battery terminal 214*a* can each be made of one or more metals and/or other electrically conductive material(s) that together form a housing of first battery 202*a*, wherein first positive battery terminal 212*a* is electrically insulated from first negative battery terminal 214*a*. Second positive battery terminal 212*b* and second negative battery terminal 214*b* can also each be made of one or more metals and/or other electrically conductive material(s) that together form a housing of second battery 202*b*, wherein second positive battery terminal 212*b* is electrically insulated from second negative battery terminal 214*b*. First and second batteries 202*a* and 202*b* can each be, e.g., a 3-volt CR2032 or similar battery.

As shown in FIG. 2, known battery holder 204 can be configured as a side-contact battery holder, and can include a first battery section 216*a* and a second battery section 216*b*. First and second battery sections 216*a* and 216*b* can be configured identically or as mirror images of each other, as shown. First battery section 216*a* can be configured to receive first battery 202*a*, and second battery section 216*b* can be configured to receive second battery 202*b* (or vice versa). First battery section 216*a* can include a first support structure 218*a* configured to hold first battery 202*a* in place, and second battery section 216*b* can include a second support structure 218*b* configured to hold second battery 202*b* in place.

Battery holder 204 can include first and second side connectors 220*a* and 220*b* and first and second bottom connectors 222*a* and 222*b*. Upon proper installation of first battery 202*a* in first support structure 218*a*, first side connector 220*a* can engage and electrically connect to a side 213*a* of first positive battery terminal 212*a*, and first bottom connector 222*a* can engage and electrically connect to a bottom 215*a* of first negative battery terminal 214*a*. Upon proper installation of second battery 202*b* in second support structure 218*b*, second side connector 220*b* can engage and electrically connect to a side 213*b* of second positive battery terminal 212*b*, and second bottom connector 222*b* can engage and electrically connect to a bottom 215*b* of second negative battery terminal 214*b*.

First and second side connectors 220*a* and 220*b* can each be electrically connected to, or integrally formed with, a positive polarity conductor 224. First and second bottom connectors 222*a* and 222*b* can each be electrically connected to, or integrally formed with, a negative polarity conductor 226. Positive polarity conductor 224 and negative polarity conductor 226 are electrically isolated from each other by a base 228 of battery holder 204. Base 228 can be made of any suitable electrically-insulating material, such as, e.g., any suitable plastic and/or rubber based material. Positive polarity conductor 224 and negative polarity conductor 226 can be coupled to respective positive and negative load terminals of a device's load.

As shown in FIG. 3, known battery holder 304 can be configured as a top-contact battery holder, and can include a first battery section 316*a* and a second battery section 316*b*. First and second battery sections 316*a* and 316*b* can be configured identically, as shown, or as mirror images of each other. First battery section 316*a* can be configured to receive first battery 202*a*, and second battery section 316*b* can be configured to receive second battery 202*b* (or vice versa). First battery section 316*a* can include a first support structure 318*a* configured to hold first battery 202*a* in place, and second battery section 316*b* can include a second support structure 318*b* configured to hold second battery 202*b* in place.

Battery holder 304 can include first and second top connectors 320*a* and 320*b* and first and second bottom connectors 322*a* and 322*b*. Upon proper installation of first battery 202*a* in first support structure 318*a*, first top connector 320*a* can engage and electrically connect to a top 317*a* of first positive battery terminal 212*a*, and first bottom connector 322*a* can engage and electrically connect to a bottom 215*a* of first negative battery terminal 214*a*. Upon proper installation of second battery 202*b* in second support structure 318*b*, second top connector 320*b* can engage and electrically connect to a top 317*b* of second positive battery terminal 212*b*, and second bottom connector 322*b* can engage and electrically connect to a bottom 215*b* of second negative battery terminal 214*b*.

First and second top connectors 320*a* and 320*b* can each be electrically connected to, or integrally formed with, a positive polarity conductor 324. First and second bottom connectors 322*a* and 322*b* can each be electrically connected to, or integrally formed with, a negative polarity conductor 326. Positive polarity conductor 324 and negative polarity conductor 326 are electrically isolated from each other by a base 328 of battery holder 304. Base 328 can be made of any suitable electrically-insulating material, such as, e.g., any suitable plastic and/or rubber based material. Positive polarity conductor 324 and negative polarity conductor 326 can be coupled to respective positive and negative load terminals of a device's load.

FIGS. 4 and 5 illustrate the adverse effects of a reverse battery connection in known battery holders 204 and 304, respectively.

As shown in FIG. 4, first battery 202*a* is improperly installed upside down in first battery section 216*a* of known battery holder 204. As a result, first side connector 220*a* and first bottom connector 222*a* are both in contact with and electrically connected to first positive battery terminal 212*a*. This reverse battery connection can cause second battery 202*b*, which is properly installed, to prematurely discharge by creating a current path (illustrated by arrows) through first positive battery terminal 212*a* and second battery 202*b* as follows: current can flow from second positive battery terminal 212*b* into second side connector 220*b*, through positive polarity conductor 224 to first side connector 220*a*. Improperly installed first battery 202*a*, which is electrically floating (because first negative battery terminal 214*a* is not electrically connected to anything), provides an electrical connection from first side connector 220*a* to first bottom connector 222*a*. Current can therefore flow from first side connector 220*a* into first bottom connector 222*a*, through negative polarity conductor 226 to second bottom connector 222*b* and into second negative battery terminal 214*b* of second battery 202*b*, completing the discharge circuit. The same adverse effect can occur if second battery 202*b* is improperly installed instead of first battery 202*a*.

Note that improper installation of both first and second batteries 202*a* and 202*b* in known side-contact battery holder 204 can cause both first and second batteries 202*a* and 202*b* to electrical float. Thus, while not causing either battery to prematurely discharge, neither battery can provide any power to a device's load.

Referring now to FIG. 5, first battery 202*a* is improperly installed upside down in first battery section 316*a* of known battery holder 304. As a result, first top connector 320*a* can be in contact with and electrically connected to first negative battery terminal 214*a*, while first bottom connector 322*a* can be in contact with and electrically connected to first positive battery terminal 212*a*. This reverse battery connection can create a short circuit that can cause both first battery 202*a* and second battery 202*b* to prematurely discharge. The improper installation of first battery 202*a* can create a current path (illustrated by arrows) through first and second batteries 202*a* and 202*b* as follows: current flow can from first positive battery terminal 212*a* of improperly installed first battery 202*a* into first bottom connector 322*a*, through negative polarity conductor 326 to second bottom connector 322*b*. Current can flow from second bottom connector 322*b* through properly installed second battery 202*b* via second negative battery terminal 214*b* and second positive battery terminal 212*b* into second top connector 320*b*. Current can flow from second top connector 320*b* through positive polarity conductor 324 to first top conductor 320*a* and into first negative battery terminal 214*a* of first battery 202*a*, completing the short circuit. The same adverse effect can occur if second battery 202*b* is improperly installed instead of first battery 202*a*.

Note that improper installation of both first and second batteries 202*a* and 202*b* in known top-contact battery holder 304, while not creating a short circuit that can prematurely discharge either battery, can cause a device's load to receive power at reverse polarity, which can damage a device's load and/or cause abnormal device operation.

Figure 6:
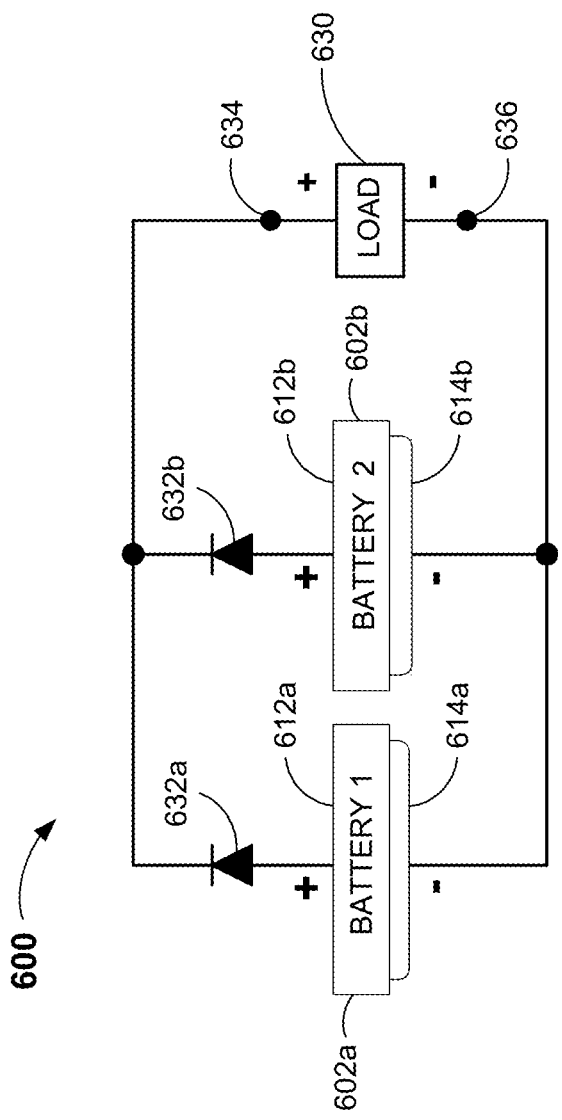
FIG. 6 illustrates a schematic circuit diagram of a known reverse battery protection circuit according to the prior art.

FIG. 6 shows a known protection circuit 600 that can be used in a device powered by a pair of parallel-coupled first and second batteries 602*a* and 602*b* in accordance with the prior art. First and second batteries 602*a* and 602*b* can be, e.g., coin or lithium cell batteries, such as, e.g., CR2032 batteries, that can power a device's load 630. Protection circuit 600 can include first and second diodes 632*a* and 632*b*, which can each be, e.g., Schottky diodes. Other types of diodes can alternatively be used. First diode 632*a* can be coupled in series between a first positive battery terminal 612*a* of battery 602*a* and a positive load terminal 634 of protection circuit 600. Second diode 632*b* can be coupled in series between a second positive battery terminal 612*b* of battery 602*b* and positive load terminal 634. A negative load terminal 636 of protection circuit 600 can be coupled to first and second negative battery terminals 614*a* and 614*b*. Load 630 can be coupled between positive load terminal 634 and negative load terminal 636.

In the event of a reverse battery connection (not shown) of, e.g., first battery 602*a* in either a side-contact battery holder or a top-contact battery holder such as, e.g., battery holders 204 and 304, respectively, first diode 632*a* can become reverse biased and can switch into a non-conductive state. This can isolate (i.e., protect) load 630 from reverse-connected first battery 602*a* and can prevent either first battery 602*a* and/or second battery 602*b* from prematurely discharging. Similarly, in the event second battery 602*b* is alternatively or additionally reverse connected, second diode 632*b* can also become reverse biased and can switch into a non-conductive state, which can isolate (i.e., protect) load 630 from reverse-connected second battery 602*b* and can prevent first battery 602*a* and/or second battery 602*b* from prematurely discharging. However, in normal device operation where both first and second diodes 632*a* and 632*b* are forward biased (i.e., in a conductive state), protection circuit 600 may not be efficient at low battery voltage. For example, assuming first and second diodes 632*a* and 632*b* each have a forward voltage of about 0.3 volts, and a CR2032 battery has a low voltage of about 1.8 volts, power losses can be as much as about 17%, which may not be acceptable in many battery-powered devices.

As is known in the art, MOSFETs have virtually no power loss when in the conductive state and, therefore, MOSFETs are sometimes used instead of diodes in devices sensitive to power losses. For example, in devices having a single battery, a P-channel MOSFET may be used instead of a diode to provide reverse battery protection. However, in devices powered by parallel-coupled batteries, simply replacing diodes, such as first and second diodes 632*a* and 632*b* of FIG. 6, with respective P-channel MOSFETs does not provide reverse battery protection, as described below in connection with FIGS. 7 and 8.

FIG. 7 shows a side-contact battery circuit 700 according to the prior art. Side-contact battery circuit 700 can include parallel-coupled first and second batteries 702*a* and 702*b* that together can power a load 730. First and second batteries 702*a* and 702*b* can each be, e.g., a coin or lithium cell battery. Side-contact battery circuit 700 can also include first and second P-channel MOSFETs 732*a* and 732*b*. First P-channel MOSFET 732*a* can be coupled in series between first battery 702*a* and a positive load terminal 734 (thus replacing first diode 632*a*), and second P-channel MOSFET 732*b* can be coupled in series between second battery 702*b* and positive load terminal 734 (thus replacing second diode 632*b*). Load 730 can be coupled between positive load terminal 734 and a negative load terminal 736.

As shown, first battery 702*a* is correctly installed and second battery 702*b* is incorrectly installed (i.e., upside down), resulting in a reverse battery connection. This reverse battery installation can result in both side connector 720*b* and bottom connector 722*b* contacting and electrically connecting to positive battery terminal 712*b*, which can cause second battery 702*b* to electrically float (because negative battery terminal 714*b* is not electrically connected to anything). The direct electrical connection from side connector 720*b* to bottom connector 722*b* via positive battery terminal 712*b* can create a current path (illustrated by arrows) that can prematurely discharge first battery 702*a*, which is correctly installed. As shown, current can flow from positive terminal 712*a* of first battery 702*a* through first and second P-channel MOSFETs 732*a* and 732*b*, which are both in a conductive state (i.e., they are both "on") because a voltage at their respective gates (designated "G") is sufficiently low relative to a voltage at their respective sources (designated "S"). Current can therefore flow through second P-channel MOSFET 732*b* into side connector 720*b* and out bottom connector 722*b* via positive battery terminal 712*b*, and into negative battery terminal 714*a* of first battery 702*a*, completing the discharge circuit. No current (or negligible current) is likely to flow into load 730, because the resistance through second P-channel MOSFET 732*b* and second battery 702*b* to negative battery terminal 714*a* is negligible, thus drawing all or substantially all of the current received at positive load terminal 734 away from load 730. The same adverse effect can occur if first battery 702*a* is improperly installed instead of second battery 702*b*. Accordingly, replacing diodes with P-channel MOSFETs as shown in side-contact battery circuit 700 does not prevent premature battery discharge in the event of a reverse battery connection.

FIG. 8 shows a top-contact battery circuit 800 according to the prior art. Top-contact battery circuit 800 can include parallel-coupled first and second batteries 802*a* and 802*b* that together can power a load 830. First and second batteries 802*a* and 802*b* can each be, e.g., a coin or lithium cell battery. Top-contact battery circuit 800 can also include first and second P-channel MOSFETs 832*a* and 832*b*. First P-channel MOSFET 832*a* can be coupled in series between first battery 702*a* and a positive load terminal 834 (thus replacing first diode 632*a*), and second P-channel MOSFET 832*b* can be coupled in series between second battery 802*b* and positive load terminal 834 (thus replacing second diode 632b). Load 830 can be coupled between positive load terminal 834 and a negative load terminal 836.

As shown, first battery 802a is correctly installed and second battery 802b is incorrectly installed (i.e., upside down), resulting in a reverse battery connection. This reverse battery installation can cause top connector 820b to contact and electrically connect to negative battery terminal 814b, while bottom connector 822b contacts and electrically connects to positive battery terminal 812b, instead of vice-versa when second battery 802b is correctly installed. This reverse battery connection results in a current path (illustrated by arrows) that can prematurely discharge both first and second batteries 802a and 802b. As shown, current can flow from positive terminal 812a of first battery 802a through first and second P-channel MOSFETs 832a and 832b, which are both in a conductive state (i.e., they are both "on") because a voltage at their respective gates (designated "G") is sufficiently low relative to a voltage at their respective sources (designated "S"). Current can therefore flow through second P-channel MOSFET 832b and reverse-connected second battery 802b and into negative battery terminal 814a of first battery 802a, completing the discharge circuit. A small amount of current received at positive load terminal 834 may flow into load 830, because the resistance through second battery 802b may not be negligible. However, that small amount of current is not likely to be sufficient to properly and/or fully drive load 830. The same adverse effect can occur if first battery 802a is improperly installed instead of second battery 802b. Accordingly, replacing diodes with P-channel MOSFETs as shown in top-contact battery circuit 800 does not prevent premature battery discharge in the event of a reverse battery connection.

Figure 9:
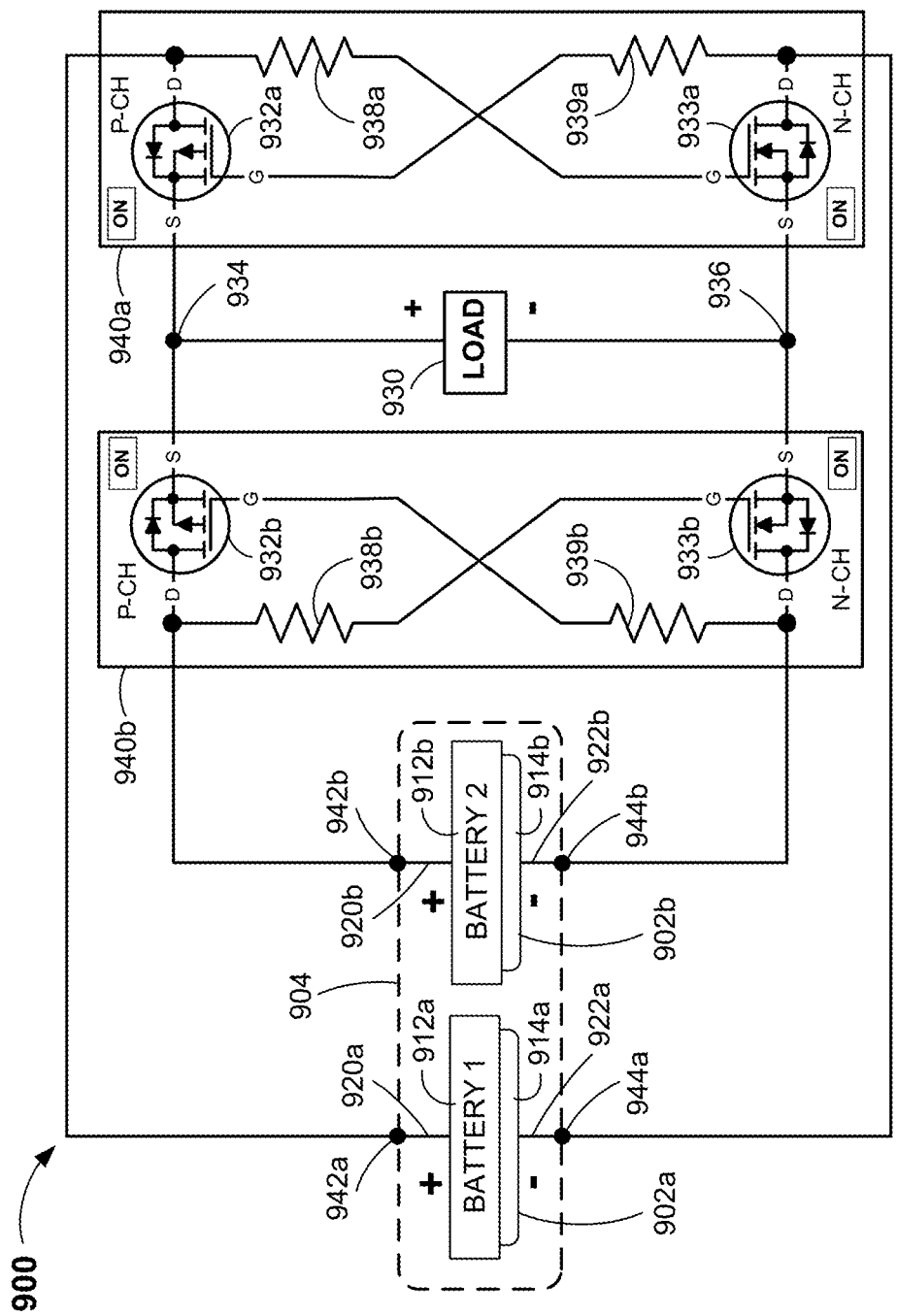
FIG. 9 illustrates a schematic circuit diagram of a reverse battery protection circuit used with a top-contact battery holder according to embodiments.

FIG. 9 shows a battery protection circuit 900 in accordance with one or more embodiments. Battery protection circuit 900 can protect a device's load 903 and/or prevent parallel-coupled first and second batteries 902a and 902b, which can be coin or lithium cell batteries, from prematurely discharging in the event of a reverse battery connection. In some embodiments, battery protection circuit 900 can be incorporated in, e.g., biosensor meter 100, and/or other suitable devices having a top-contact battery holder such as, e.g., battery holder 304. In some embodiments, battery protection circuit 900 can be integrated with a device's load circuitry or, alternatively, integrated with a battery holder incorporated in a battery-powered device. In other embodiments, battery protection circuit 900 can be incorporated in a device as a discrete circuit (e.g., in the form of an integrated circuit chip and/or module) coupled between a top-contact battery holder and a load. Battery protection circuit 900 can alternatively be incorporated in a device in other suitable ways.

As shown in FIG. 9, battery protection circuit 900 can in some embodiments include a pair of battery protection cells 940a and 940b, which can be identical to each other. Battery protection cell 940a can include a first P-channel MOSFET 932a and a first N-channel MOSFET 933a, each of which can be an enhancement-mode type MOSFET in some embodiments. In other embodiments, first MOSFETs 932a and 933a can each be other suitable types of FETs (field effect transistors). The source (designated "S") of first P-channel MOSFET 932a can be coupled to a positive load terminal 934, and the source of first N-channel MOSFET 933a can be coupled to a negative load terminal 936. Load 930 can be coupled between positive load terminal 934 and negative load terminal 936. The drain (designated "D") of first P-channel MOSFET 932a can be coupled to a positive battery terminal connector 942a and to the gate (designated "G") of first N-channel MOSFET 933a. The drain of first N-channel MOSFET 933a can be coupled to a negative battery terminal connector 944a and to the gate of first P-channel MOSFET 932a. In some embodiments, resistive elements (e.g., resistors) can optionally be coupled in series between a battery terminal and a MOSFET gate to protect against electrostatic discharge (ESD). For example, in some embodiments, resistor 938a can be coupled between the gate of first N-channel MOSFET 933a and positive battery terminal connector 942a, and resistor 939a can be coupled between the gate of first P-channel MOSFET 932a and negative battery terminal connector 944a. In some embodiments, values for resistors 938a and 939a can range from about 10 k ohms to about 3M ohms.

In some embodiments, positive battery terminal connector 942a can be electrically connected to a top connector 920a of battery holder 904, while negative battery terminal connector 944a can be electrically connected to bottom connector 922a of battery holder 904. In other embodiments, positive battery terminal connector 942a can be integrally formed with top connector 920a of battery holder 904, while negative battery terminal connector 944a can be integrally formed with bottom connector 922a of battery holder 904.

Battery protection cell 940b, which in this embodiment is configured identically as battery protection cell 940a, can include a second P-channel MOSFET 932b and a second N-channel MOSFET 933b, each of which can be an enhancement-mode type MOSFET in some embodiments. In other embodiments, MOSFETs 932b and 933b can each be other suitable types of FETs. The source (designated "S") of second P-channel MOSFET 932b can be coupled to positive load terminal 934, and the source of second N-channel MOSFET 933b can be coupled to negative load terminal 936. The drain (designated "D") of second P-channel MOSFET 932b can be coupled to a positive battery terminal connector 942b and to the gate (designated "G") of second N-channel MOSFET 933b. The drain of second N-channel MOSFET 933b can be coupled to a negative battery terminal connector 944b and to the gate of second P-channel MOSFET 932b. In some embodiments, resistor 938b can optionally be coupled between the gate of second N-channel MOSFET 933b and positive battery terminal connector 942b, and resistor 939b can be coupled between the gate of second P-channel MOSFET 932b and negative battery terminal connector 944b. Resistors 938b and 939b can be used to protect against ESD. In some embodiments, values for resistors 938b and 939b can range from about 10 k ohms to about 3M ohms.

In some embodiments, positive battery terminal connector 942b can be electrically connected to a top connector 920b of battery holder 904, while negative battery terminal connector 944b can be electrically connected to bottom connector 922b of battery holder 904. In other embodiments, positive battery terminal connector 942b can be integrally formed with top connector 920b of battery holder 904, while negative battery terminal connector 944b can be integrally formed with bottom connector 922b of battery holder 904.

In alternative embodiments, battery protection circuit 900 can include only one or more than two battery protection cells 940a and/or 940b depending on the number of parallel-coupled batteries in the device. For example, in devices having more than two parallel-coupled batteries, a respective battery protection cell 940a or 940b can be coupled to each parallel-coupled battery to provide protection against a reverse battery connection. In devices having only a single battery, one of battery protection cells 940a or 940b can be coupled to that battery to provide protection against a reverse battery connection. Furthermore, in devices utilizing other (e.g., non-battery) sources of power, a single battery protection cell 940a or 940b can be used to provide protection against a reverse polarity power connection.

In normal operation, first and second batteries 902a and 902b are properly installed as shown in FIG. 9. That is, first positive battery terminal connector 942a is electrically coupled to positive battery terminal 912a, first negative battery terminal connector 944a is electrically coupled to negative battery terminal 914a, second positive battery terminal connector 942b is electrically coupled to positive battery terminal 912b, and second negative battery terminal connector 944b is electrically coupled to negative battery terminal 914b. First and second P-channel MOSFETs 932a and 932b can both be in a conductive state (i.e., they are "on"), because a voltage at their respective gates is sufficiently low relative to a voltage at their respective sources. First and second N-channel MOSFETS 933a and 933b can also both be in a conductive state (i.e., they are "on"), because a voltage at their respective gates is sufficiently high relative to a voltage at their respective sources. Current can therefore flow from first and second batteries 902a and 902b through respective first and second P-channel MOSFETs 932a and 932b to positive load terminal 934 and into load 930.

Figure 10:
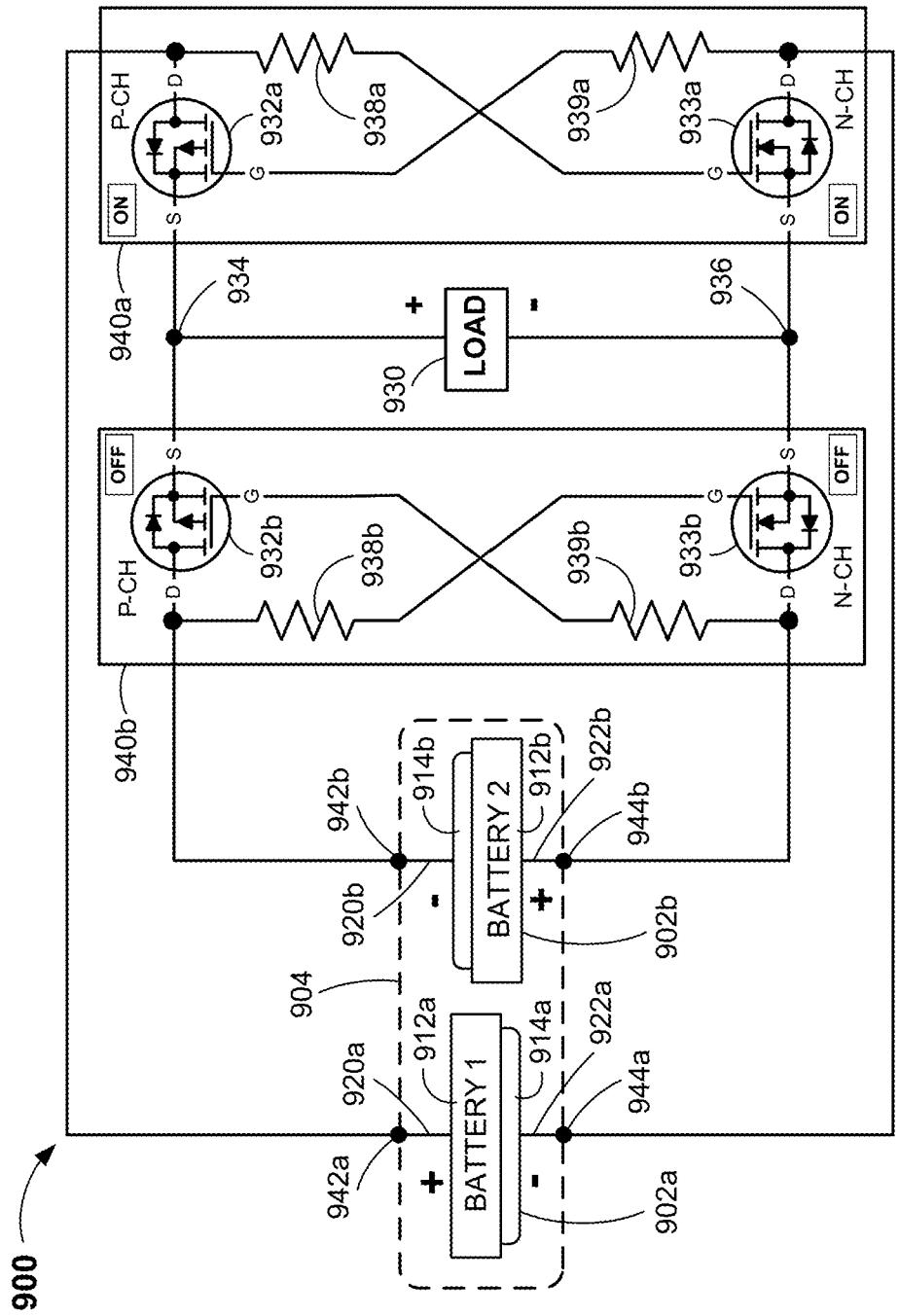
FIG. 10 illustrates a schematic circuit diagram of the reverse battery protection circuit of FIG. 9 used with a top-contact battery holder having a reverse-connected battery.

In the event of a reverse battery connection wherein, e.g., second battery 902b is incorrectly installed (e.g., upside down in the case of a coin or lithium cell battery), as shown in FIG. 10, positive battery terminal connector 942b can be electrically coupled to negative battery terminal 914b, and negative battery terminal connector 944b can be electrically coupled to positive battery terminal 912b. This reverse battery connection can cause second P-channel MOSFET 932b to switch into a non-conductive state (i.e., to turn "off"), because the voltage at the gate of second P-channel MOSFET 932b, which is received from positive voltage terminal 912b of second battery 902b, is no longer sufficiently low to keep second P-channel MOSFET 932b on, but is instead high relative to the voltage at the source of second P-channel MOSFET 932b. This reverse battery connection also can cause second N-channel MOSFET 933b to switch into a non-conductive state (i.e., to turn "off"), because the voltage at the gate of second N-channel MOSFET 933b, which is received from negative voltage terminal 914b of second battery 902b, is no longer sufficiently high to keep second N-channel MOSFET 933b on, but is instead low relative to the voltage at the source of second N-channel MOSFET 933b. With both second P-channel MOSFET 932b and second N-channel MOSFET 933b turned off, load 930 can therefore be protected (i.e., isolated) from reverse-connected second battery 902b, while first battery 902a can continue to provide power to load 930, albeit not necessarily enough for load 930 to properly operate. Furthermore, neither first battery 902a nor second battery 902b is subject to premature discharge as a result of a reverse battery connection.

In the event that first battery 902a is incorrectly installed instead of second battery 902b, battery protection cell 940a can provide the same load and premature battery discharge protection as battery protection cell 940b described above. And in the event that both first and second batteries 902a and 902b are incorrectly installed, both battery protection cells 940a and 940b can operate to isolate load 930 and prevent premature battery discharge as described above for battery protection cell 940b.

Although described above in connection with coin or lithium cell batteries, battery protection circuit 900 can be used in devices powered by other types of suitable batteries where incorrect battery installation can result in a reverse polarity connection (i.e., a positive battery terminal connector electrically coupled to a negative battery terminal and a negative battery terminal connector electrically coupled to a positive battery connector).

Figure 11:
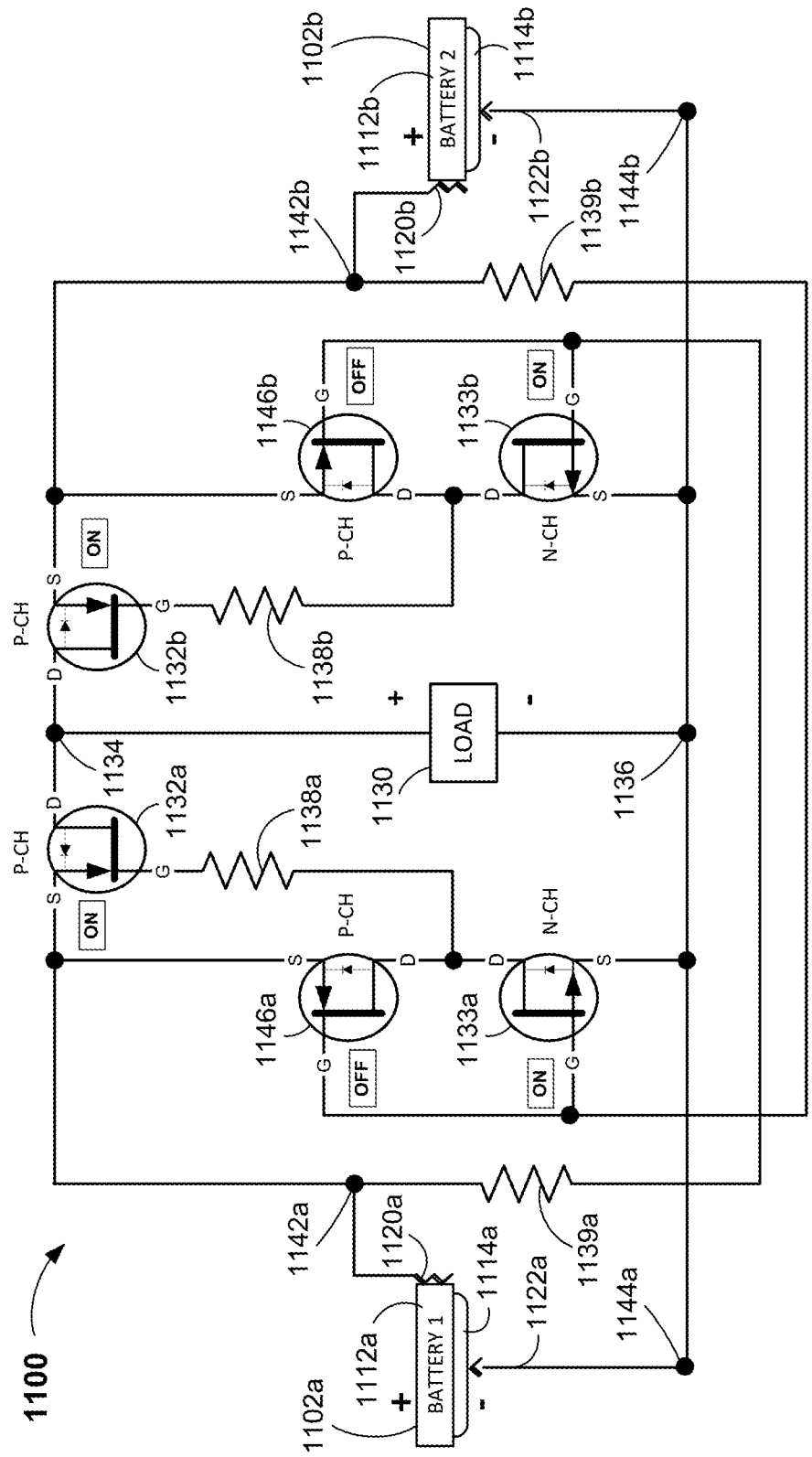
FIG. 11 illustrates a schematic circuit diagram of a reverse battery protection circuit used with a side-contact battery holder according to embodiments.

FIG. 11 shows another battery protection circuit 1100 in accordance with one or more embodiments. Battery protection circuit 1100 can protect a device's load 1130 and prevent one or both parallel-coupled first and second batteries 1102a and 1102b from prematurely discharging in the event of a reverse battery connection. In some embodiments, battery protection circuit 1100 can be incorporated in, e.g., biosensor meter 100, and/or other suitable devices having a side-contact battery holder such as, e.g., battery holder 204. In some embodiments, battery protection circuit 1100 can be integrated with a device's load circuitry or, alternatively, integrated with a battery holder incorporated in a battery-powered device. In other embodiments, battery protection circuit 1100 can be incorporated in a device as a discrete circuit (e.g., in the form of an integrated circuit chip and/or module) coupled between a side-contact battery holder and a load. Battery protection circuit 1100 can alternatively be incorporated in a device in other suitable ways.

As shown in FIG. 11, battery protection circuit 1100 can include a first P-channel MOSFET 1132a, a second P-channel MOSFET 1146a, and a first N-channel MOSFET 1133a, each of which can be an enhancement-mode type MOSFET in some embodiments. In other embodiments, MOSFETs 1132a, 1146a, and 1133a can each be other suitable types of FETs. The drain (designated "D") of first P-channel MOSFET 1132a can be coupled to a positive load terminal 1134, and the source (designated "S") of first N-channel MOSFET 1133a can be coupled to a negative load terminal 1136. Load 1130 can be coupled between positive load terminal 1134 and negative load terminal 1136. The gate (designated "G") of first P-channel MOSFET 1132a can be coupled to the drain of second P-channel MOSFET 1146a and to the drain of first N-channel MOSFET 1133a. The source of first P-channel MOSFET 1132a can be coupled to the source of second P-channel MOSFET 1146a and to a first positive battery terminal connector 1142a. First positive battery terminal connector 1142a can be electrically connected to a side connector 1120a or, in alternative embodiments, integrally formed with side connector 1120a. The gate of second P-channel MOSFET 1146a can be coupled to the gate of first N-channel MOSFET 1133a and to a second positive battery terminal connector 1142b. Second positive battery terminal connector 1142b can be electrically connected to a side connector 1120b or, in alternative embodiments, integrally formed with side connector 1120b. The source of first N-channel MOSFET 1133a can be coupled to a first negative battery terminal connector 1144a. First negative battery terminal connector 1144a can be electrically connected to a bottom connector 1122a or, in alternative embodiments, integrally formed with bottom connector 1122a.

Battery protection circuit 1100 can also include a third P-channel MOSFET 1132b, a fourth P-channel MOSFET 1146b, and a second N-channel MOSFET 1133b, each of which can be an enhancement-mode type MOSFET in some embodiments. In other embodiments, MOSFETs 1132b, 1146b, and 1133b can each be other suitable types of FETs. The drain (designated "D") of third P-channel MOSFET 1132b can be coupled to positive load terminal 1134, and the source (designated "S") of second N-channel MOSFET 1133b can be coupled to negative load terminal 1136. The gate (designated "G") of third P-channel MOSFET 1132b can be coupled to the drain of fourth P-channel MOSFET 1146b and to the drain of second N-channel MOSFET 1133b. The source of third P-channel MOSFET 1132b can be coupled to the source of fourth P-channel MOSFET 1146b and to second positive battery terminal connector 1142b. The gate of fourth P-channel MOSFET 1146b can be coupled to the gate of second N-channel MOSFET 1133b and to first positive battery terminal connector 1142a. The source of second N-channel MOSFET 1133b can be coupled to a second negative battery terminal connector 1144b. Second negative battery terminal connector 1144b can be electrically connected to a bottom connector 1122b or, in alternative embodiments, integrally formed with bottom connector 1122b.

In some embodiments of battery protection circuit 1100, resistors can optionally be coupled in series to the MOSFET gates to protect against electrostatic discharge (ESD). For example, in some embodiments, resistor 1138a can be coupled between the gate of first P-channel MOSFET 1132a and the drains of second P-channel MOSFET 1146a and first N-channel MOSFET 1133a. Resistor 1139a can be coupled between first positive battery terminal connector 1142a to the gates of fourth P-channel MOSFET 1146b and second N-channel MOSFET 1133b. Resistor 1138b can be coupled between the gate of third P-channel MOSFET 1132b and the drains of fourth P-channel MOSFET 1146b and second N-channel MOSFET 1133b. Resistor 1139b can be coupled between second positive battery terminal connector 1142b to the gates of second P-channel MOSFET 1146a and first N-channel MOSFET 1133a. In some embodiments, values for resistors 1138a, 1138b, 1139a, and 1139b can range from about 10 k ohms to about 3M ohms.

In normal operation, first and second batteries 1102a and 1102b are properly installed as shown in FIG. 11. That is, first positive battery terminal connector 1142a can be electrically coupled to positive battery terminal 1112a, first negative battery terminal connector 1144a can be electrically coupled to negative battery terminal 1114a, second positive battery terminal connector 1142b can be electrically coupled to positive battery terminal 1112b, and second negative battery terminal connector 1144b can be electrically coupled to negative battery terminal 1114b. As a result, both second and fourth P-channel MOSFETs 1146a and 1146b can be in a non-conductive state (i.e., they are "off"), because a voltage at their respective gates received from second positive battery terminal 1112b and first positive battery terminal 1112a, respectively, is not sufficiently low relative to a voltage at their respective sources to turn on the second and fourth P-channel MOSFETs 1146a and 1146b. Both first and second N-channel MOSFETS 1133a and 1133b can be in a conductive state (i.e., they are "on"), because a voltage at their respective gates also received from second positive battery terminal 1112b and first positive battery terminal 1112a, respectively, is sufficiently high relative to a voltage at their respective sources. This can allow both first and third P-channel MOSFETs 1132a and 1132b to be in a conductive state (i.e., they are "on"), because a voltage at their respective gates is sufficiently low relative to a voltage at their respective sources. Current can therefore flow from first and second batteries 1102a and 1102b through respective first and third P-channel MOSFETs 1132a and 1132b to positive load terminal 1134 and into load 1130.

Figure 12:
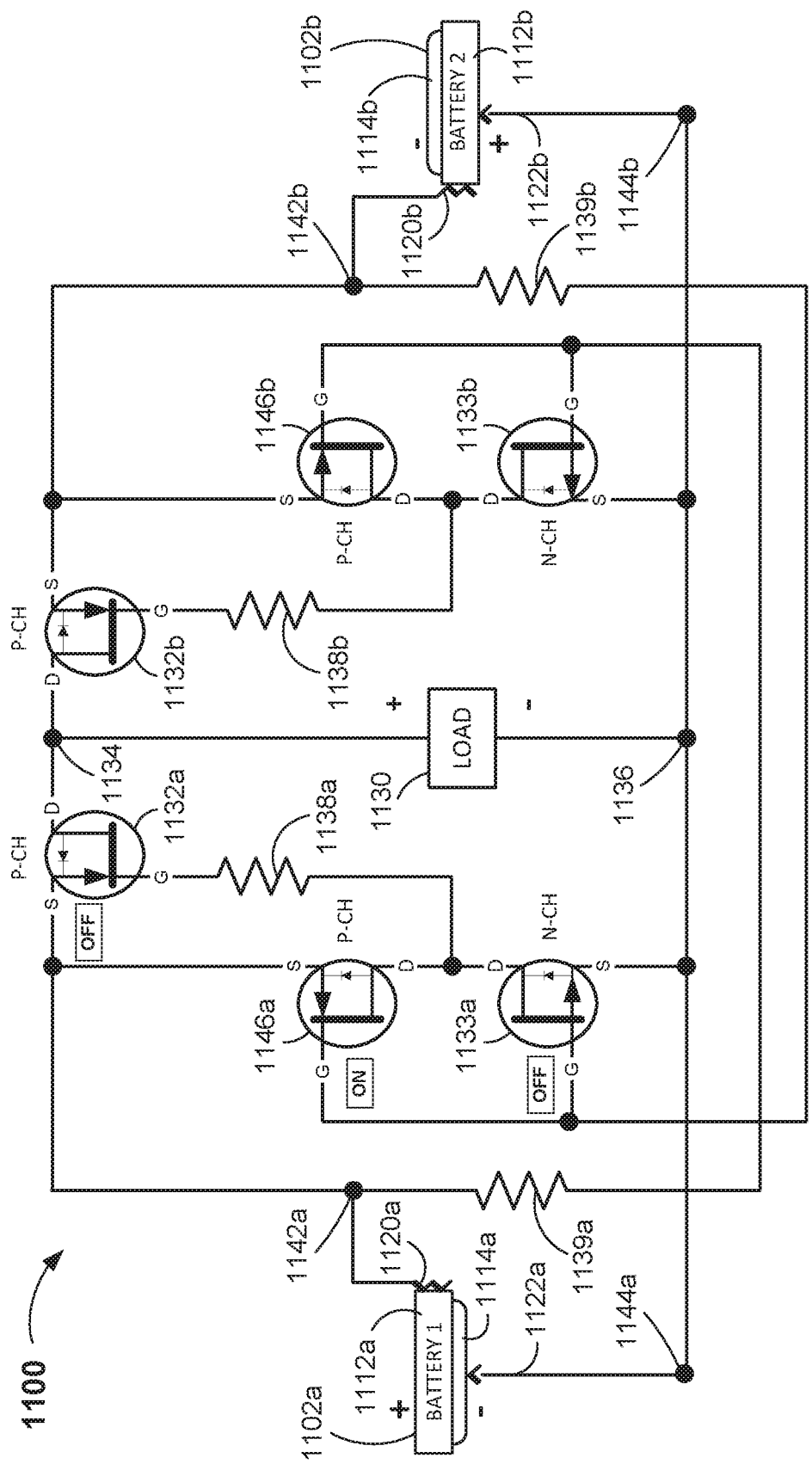
FIG. 12 illustrates a schematic circuit diagram of the reverse battery protection circuit of FIG. 11 used with a side-contact battery holder having a reverse-connected battery.

In the event of a reverse battery connection wherein, e.g., second battery 1102b is incorrectly installed (e.g., upside down in the case of a coin or lithium cell battery), as shown in FIG. 12, second positive battery terminal connector 1142b and second negative battery terminal connector 1144b can both be electrically coupled to second positive battery terminal 1112b. This incorrect installation of second battery 1102b can cause second battery 1102b to electrically float, because second negative battery terminal 1114b is not electrically connected to any part of battery protection circuit 1100. Therefore, incorrectly installed second battery 1102b can provide no power and serves only to connect together second positive battery terminal connector 1142b and second negative battery terminal connector 1144b.

As a result, second P-channel MOSFET 1146a can turn on, because a voltage at the gate of second P-channel MOSFET 1146a received from first negative battery terminal 1114a is sufficiently low relative to a voltage at the source of second P-channel MOSFET 1146a to cause second P-channel MOSFET 1146a to switch into a conductive state. First N-channel MOSFET 1133a can turn off, because its gate voltage is also received from first negative battery terminal 1114a, which is not sufficiently high relative to a voltage at the source of first N-channel MOSFET 1133a to keep on first N-channel MOSFET 1133a. With first N-channel MOSFET 1133a turned off, first P-channel MOSFET 1132a can also turn off, because its gate voltage is high (via turned on second P-channel MOSFET 1146a and first positive battery terminal 1112a) and is no longer sufficiently low relative to its source voltage to remain in a conductive state. Because the source of third P-channel MOSFET 1132b is now electrically coupled to first negative battery terminal 1114a via the connection between second positive battery terminal connector 1142b and second negative battery terminal connector 1144b, third P-channel MOSFET 1132b can also turn off, because its gate voltage is also no longer sufficiently low relative to its source voltage to remain in a conductive state. Fourth P-channel MOSFET 1146b can remain off, because a voltage at the gate of fourth P-channel MOSFET 1146b can continue to be received from first positive battery terminal 1112a. Similarly, the voltage at the gate of second N-channel MOSFET 1133b can continue to be high via first positive battery terminal 1112a. However, because battery 1102b provides no power via its incorrect installation, the conductive states of third P-channel MOSFET 1132b, fourth P-channel MOSFET 1146b, and second N-channel MOSFET 1133b can be irrelevant and all can be considered to be in a non-conductive state. Thus, with first and third P-channel MOSFETs 1132a and 1132b turned off, load 1130 can therefore be protected (i.e., isolated) from incorrectly installed second battery 1102b, and correctly-installed first battery 1102a cannot prematurely discharge, because there is no discharge current path through battery protection circuit 1100.

In the event that first battery 1102a is incorrectly installed instead of second battery 1102b, battery protection circuit 1100 can operate substantially identically as described above to protect load 1130 and prevent premature battery discharge, except that second P-channel MOSFET 1146a would be off and fourth P-channel MOSFET 1146b would be on.

Figure 13:
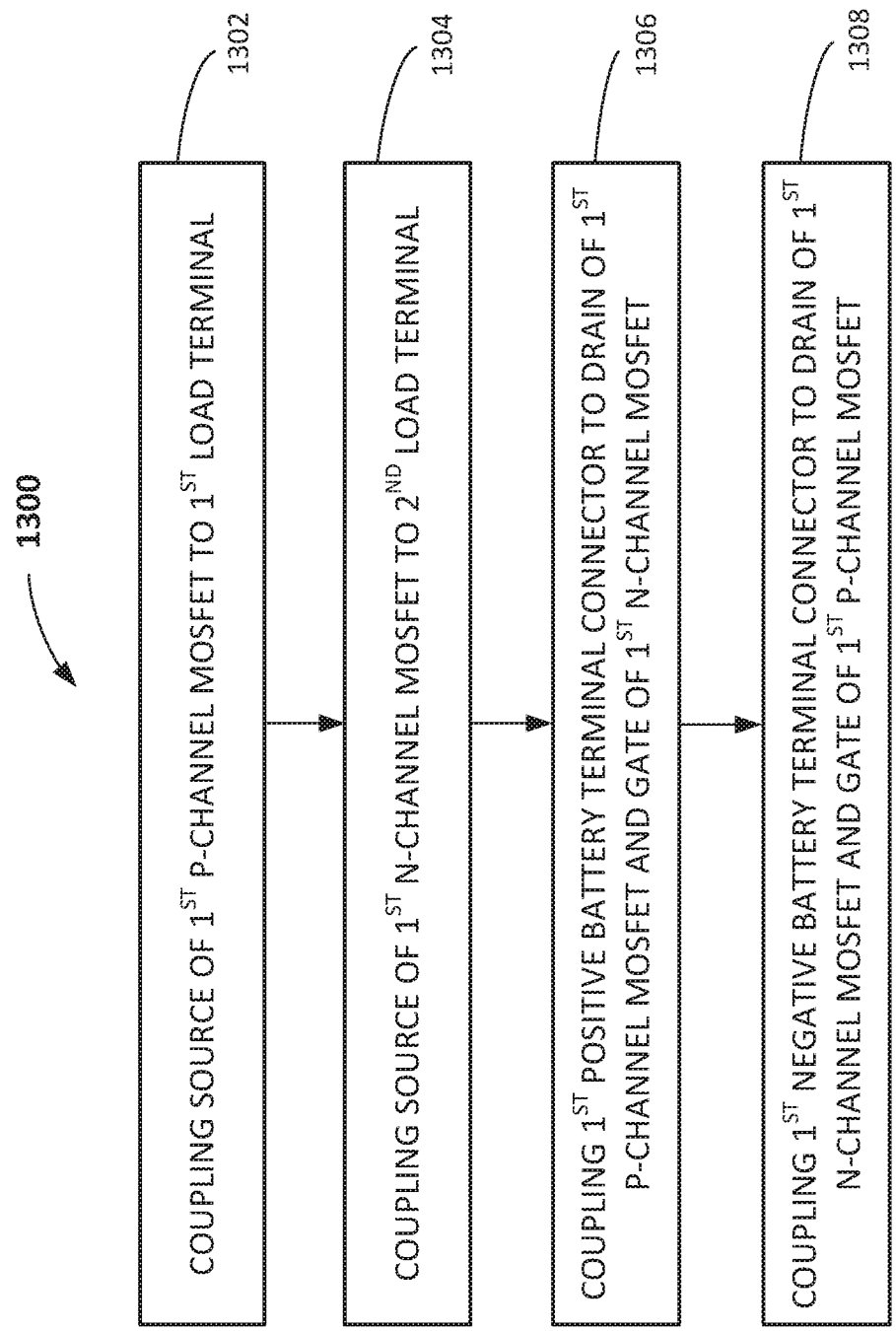
FIG. 13 illustrates a flowchart of a method of protecting a load from a reverse battery connection according to embodiments.

FIG. 13 illustrates a method 1300 of protecting a load from a reverse battery connection in accordance with one or more embodiments. Method 1300 can be used in connection with devices powered by a single battery or power source, and/or two or more batteries coupled in parallel, installed in a top-contact battery holder, such as, e.g., battery holder 304 of FIG. 3. At process block 1302, method 1300 can include coupling a source of a first P-channel MOSFET to a first load terminal. For example, referring to FIG. 9, the source of first P-channel MOSFET 932a can be coupled to positive load terminal 934.

At process block 1304, method 1300 can include coupling a source of a first N-channel MOSFET to a second load terminal. Again referring to FIG. 9, e.g., the source of first N-channel MOSFET 933a can be coupled to negative load terminal 936.

At process block 1306, a first positive battery terminal connector can be coupled to a drain of the first P-channel MOSFET and to a gate of the first N-channel MOSFET. For example, first positive battery terminal connector 942a can be coupled to a drain of first P-channel MOSFET 932a and to a gate of first N-channel MOSFET 933a, as shown in FIG. 9. In some embodiments, process block 1306 can optionally include coupling a resistive element between the first positive battery terminal connector and the gate of the first N-channel MOSFET, such as, e.g., coupling resistor 938a between first positive battery terminal connector 942a and the gate of first N-channel MOSFET 933a, to provide protection against ESD.

At process block 1308, method 1300 can include coupling a first negative battery terminal connector to a drain of the first N-channel MOSFET and to a gate of the first P-channel MOSFET. For example, as shown in FIG. 9, first negative battery terminal connector 944a can be coupled to a drain of first N-channel MOSFET 933a and to a gate of first P-channel MOSFET 932a. In some embodiments, process block 1308 can optionally include coupling a resistive element between the first negative battery terminal connector and the gate of the first P-channel MOSFET, such as, e.g., coupling resistor 939a between first negative battery terminal connector 944a and the gate of first P-channel MOSFET 932a, to provide protection against ESD.

Figure 14:
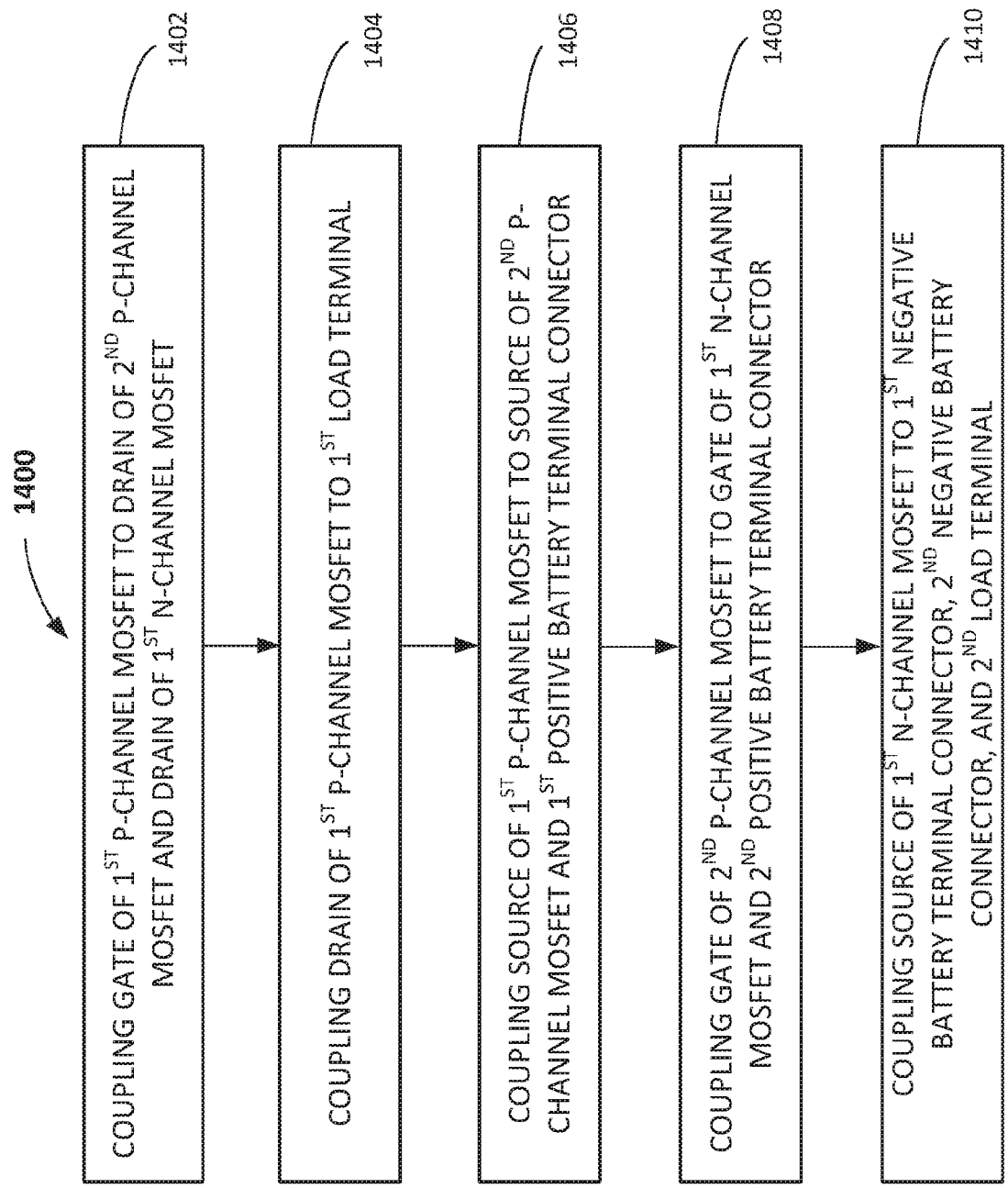
FIG. 14 illustrates a flowchart of another method of protecting a load from a reverse battery connection according to embodiments.

FIG. 14 illustrates another method 1400 of protecting a load from a reverse battery connection in accordance with one or more embodiments. Method 1400 can be used in connection with devices powered by two parallel-coupled batteries installed in a side-contact battery holder, such as, e.g., battery holder 204 of FIG. 2. At process block 1402, method 1400 can include coupling a gate of a first P-channel MOSFET to a drain of a second P-channel MOSFET and to a drain of a first N-channel MOSFET. For example, referring to FIG. 11, the gate of first P-channel MOSFET 1132a can be coupled to the drain of second P-channel MOSFET 1146a and to the drain of first N-channel MOSFET 1133a.

At process block 1404, method 1400 can include coupling a drain of the first P-channel MOSFET to a first load terminal. Again referring to FIG. 11, e.g., a drain of first P-channel MOSFET 1132a can be coupled to a positive load terminal 1134.

At process block 1406, a source of the first P-channel MOSFET can be coupled to a source of the second P-channel MOSFET and to a first positive battery terminal connector. For example, a source of first P-channel MOSFET 1132a can be coupled to a source of second P-channel MOSFET 1146a and to first positive battery terminal connector 1142a, as shown in FIG. 11.

At process block 1408, a gate of the second P-channel MOSFET can be coupled to a gate of the first N-channel MOSFET and to a second positive battery terminal connector. As also shown in FIG. 11, e.g., a gate of second P-channel MOSFET 1146a can be coupled to a gate of first N-channel MOSFET 1133a and to a second positive battery terminal connector 1142b.

At process block 1410, method 1400 can include coupling a source of the first N-channel MOSFET to a first negative battery terminal connector, to a second negative battery terminal connector, and to a second load terminal. For example, again referring to FIG. 11, a source of first N-channel MOSFET 1133a can be coupled to first negative battery terminal connector 1144a, to second negative battery terminal connector 1144b, and to second load terminal 1136.

The above process blocks of method 1300 and/or method 1400 can be executed or performed in an order or sequence not limited to the order and sequence shown and described. For example, in some embodiments, process blocks 1302, 1304, 1306, and 1308 and/or process blocks 1402, 1404, 1406, 1408, and 1410 can performed substantially simultaneously as part of an integrated circuit fabrication process.

Persons skilled in the art should readily appreciate that the invention described herein is susceptible of broad utility and application. Many embodiments and adaptations of the invention other than those described herein, as well as many variations, modifications, and equivalent arrangements, will be apparent from, or reasonably suggested by, the invention and the foregoing description thereof, without departing from the substance or scope of the invention. For example, although described in connection with a battery-powered biosensor meter and coin type batteries, one or more embodiments of the invention may be used with other types of batteries and other types of devices powered by batteries coupled in parallel and sensitive to battery polarity. Accordingly, while the invention has been described herein in detail in relation to specific embodiments, it should be understood that this disclosure is only illustrative and presents examples of the invention and is made merely for purposes of providing a full and enabling disclosure of the invention. This disclosure is not intended to limit the invention to the particular apparatus, devices, assemblies, systems or methods disclosed, but, to the contrary, the intention is to cover all modifications, equivalents, and alternatives falling within the scope of the invention.

What is claimed is:

1. A battery-powered biosensor meter comprising:
a microcontroller configured to determine a property of an analyte in a fluid;
a memory coupled to the microcontroller to store measurement results;
a battery holder configured to receive a plurality of batteries;
a reverse battery protection circuit coupled to the battery holder, the microcontroller, and the memory; and
a housing configured to house the microcontroller, the memory, the battery holder, and the reverse battery protection circuit,
wherein the reverse battery protection circuit includes:
a first P-channel MOSFET having a gate, a drain, and a source;
a second P-channel MOSFET having a gate, a drain coupled to the gate of the first P-channel MOSFET, and a source coupled to the source of the first P-channel MOSFET;
a first N-channel MOSFET having a gate coupled to the gate of the second P-channel MOSFET, a drain coupled to the drain of the second P-channel MOSFET and to the gate of the first P-channel MOSFET, and a source;
a first load terminal coupled to the drain of the first P-channel MOSFET;
a first positive battery terminal connector coupled to the source of the first P-channel MOSFET and to the source of the second P-channel MOSFET, the first positive battery terminal connector configured to electrically connect to a first battery terminal;

a second positive battery terminal connector coupled to the gate of the first N-channel MOSFET and to the gate of the second P-channel MOSFET, the second positive battery terminal connector configured to electrically connect to a second battery terminal;

a first negative battery terminal connector configured to electrically connect to a third battery terminal;

a second negative battery terminal connector configured to electrically connect to a fourth battery terminal; and a second load terminal; wherein:

the first negative battery terminal, the second negative battery terminal, the second load terminal, and the source of the first N-channel MOSFET are coupled to each other.

2. The meter of claim 1 wherein the first positive battery terminal connector of the reverse battery protection circuit has a top contact configuration.

3. The meter of claim 1 wherein the reverse battery protection circuit further includes:

a first resistive element coupled in series between the first positive battery terminal connector and the gate of the first N-channel MOSFET; and a second resistive element coupled in series between the first negative battery terminal connector and the gate of the first P-channel MOSFET.

4. The meter of claim 1 wherein the reverse battery protection circuit further includes:

a second P-channel MOSFET having a drain, a gate, and a source coupled to the first load terminal;

a second N-channel MOSFET having a drain, a gate, and a source coupled to the second load terminal;

a second positive battery terminal connector coupled to the drain of the second P-channel MOSFET and to the gate of the second N-channel MOSFET, the second positive battery terminal connector configured to electrically connect to a third battery terminal; and a second negative battery terminal connector coupled to the drain of the second N-channel MOSFET and to the gate of the second P-channel MOSFET, the second negative battery terminal connector configured to electrically connect to a fourth battery terminal.

5. The meter of claim 4 wherein the second positive battery terminal connector of the reverse battery protection circuit has a top contact configuration.

6. The meter of claim 4 wherein the reverse battery protection circuit further includes:

a third resistive element coupled in series between the second positive battery terminal connector and the gate of the second N-channel MOSFET; and a fourth resistive element coupled in series between the first negative battery terminal connector and the gate of the second P-channel MOSFET.

7. The meter of claim 4 wherein:

the first positive battery terminal connector and the first negative battery terminal connector of the reverse battery protection circuit are configured to electrically connect to respective battery terminals of a first battery; and the second positive battery terminal connector and the second negative battery terminal connector of the reverse battery protection circuit are configured to electrically connect to respective battery terminals of a second battery.

8. A reverse battery protection circuit comprising:

a first P-channel MOSFET having a gate, a drain, and a source;

a second P-channel MOSFET having a gate, a drain coupled to the gate of the first P-channel MOSFET, and a source coupled to the source of the first P-channel MOSFET;

a first N-channel MOSFET having a gate coupled to the gate of the second P-channel MOSFET, a drain coupled to the drain of the second P-channel MOSFET and to the gate of the first P-channel MOSFET, and a source;

a first load terminal coupled to the drain of the first P-channel MOSFET; and a first positive battery terminal connector coupled to the source of the first P-channel MOSFET and to the source of the second P-channel MOSFET, the first positive battery terminal connector configured to electrically connect to a first battery terminal.

9. A method of protecting a load from a reverse battery connection, the method comprising:

coupling a source of a first P-channel MOSFET to a first load terminal;

coupling a source of a first N-channel MOSFET to a second load terminal;

coupling a first positive battery terminal connector to a drain of the first P-channel MOSFET and to a gate of the first N-channel MOSFET, the first positive battery terminal configured to electrically connect to a first battery terminal;

coupling a first negative battery terminal connector to a drain of the first N-channel MOSFET and to a gate of the first P-channel MOSFET, the first negative battery terminal configured to electrically connect to a second battery terminal;

coupling a source of a second P-channel MOSFET to the first load terminal;

coupling a source of a second N-channel MOSFET to the second load terminal; and coupling a second positive battery terminal connector to a drain of the second P-channel MOSFET and to a gate of the second N-channel MOSFET, the second positive battery terminal connector configured to electrically connect to a third battery terminal.

10. The method of claim 9 further comprising:

coupling a second negative battery terminal connector to a drain of the second N-channel MOSFET and to a gate of the second P-channel MOSFET, the second negative battery terminal connector configured to electrically connect to a fourth battery terminal.

11. The method of claim 10 further comprising providing a battery holder configured to receive the first positive battery terminal connector and the first negative battery connector, wherein the first positive battery terminal connector has a top contact configuration.

12. The reverse battery protection circuit of claim 8 further comprising:

a second positive battery terminal connector coupled to the gate of the first N-channel MOSFET and to the gate of the second P-channel MOSFET, the second positive battery terminal connector configured to electrically connect to a second battery terminal;

a first negative battery terminal connector configured to electrically connect to a third battery terminal;

a second negative battery terminal connector configured to electrically connect to a fourth battery terminal; and a second load terminal; wherein:

the first negative battery terminal, the second negative battery terminal, the second load terminal, and the source of the first N-channel MOSFET are coupled to each other.

13. The reverse battery protection circuit of claim 12 wherein the first positive battery terminal connector has a top contact configuration.

14. The reverse battery protection circuit of claim 12 further comprising: a first resistive element coupled in series between the first positive battery terminal connector and the gate of the first N-channel MOSFET; and a second resistive element coupled in series between the first negative battery terminal connector and the gate of the first P-channel MOSFET.

* * * * *